(12) United States Patent
Dahlqvist et al.

(10) Patent No.: US 10,017,309 B2
(45) Date of Patent: Jul. 10, 2018

(54) PACKAGING UNIT FOR HYGIENE ARTICLES AND A METHOD OF FORMING A PACKAGING UNIT

(71) Applicant: SCA Hygiene Products AB, Göteborg (SE)

(72) Inventors: Conny Dahlqvist, Göteborg (SE); Ulrika Persson, Göteborg (SE); Sofia Ekstedt, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 15/318,020

(22) PCT Filed: Jun. 13, 2014

(86) PCT No.: PCT/SE2014/050726
§ 371 (c)(1),
(2) Date: Dec. 12, 2016

(87) PCT Pub. No.: WO2015/190970
PCT Pub. Date: Dec. 17, 2015

(65) Prior Publication Data
US 2017/0190489 A1    Jul. 6, 2017

(51) Int. Cl.
*A61F 13/551* (2006.01)
*B65D 75/20* (2006.01)
(Continued)

(52) U.S. Cl.
CPC ........ *B65D 75/20* (2013.01); *A61F 13/15739* (2013.01); *A61F 13/15747* (2013.01);
(Continued)

(58) Field of Classification Search
CPC ............... A61F 13/15739; A61F 13/55135
See application file for complete search history.

(56) References Cited

U.S. PATENT DOCUMENTS 3,217,871 A * 11/1965 Lee ................... B65D 75/30
                                                   206/440
3,913,580 A    10/1975 Ginocchio
(Continued)

FOREIGN PATENT DOCUMENTS

EP       0 368 914 A1    5/1990
EP       0 841 049 A1    5/1998
(Continued)

OTHER PUBLICATIONS

Office Action (Notice of Reasons for Rejection) dated Nov. 13, 2017, by the Japanese Patent Office in corresponding Japanese Patent Application No. 2016-572472 and English Translation of the Office Action. (6 pages).

(Continued)

*Primary Examiner* — Paula L Craig
(74) *Attorney, Agent, or Firm* — Buchanan Ingersoll & Rooney PC

(57) ABSTRACT

A packaging unit for hygiene articles that is formed from a sheet of material having an inner surface comprises an edge zone comprising an inner edge portion and an outer edge portion. At least one of the outer and inner edge portions comprises at least one region provided with a resealable adhesive. The sheet has at least one folding axis dividing said sheet into a first and second regions region. The sheet is folded about said at least one folding axis with said first and second regions in an overlapping configuration, thereby providing a packaging unit. Overlapping outer edge portions of the sheet layers are at least partly adhesive-free and are at least partially connected to each other by a mechanical interaction providing a sealing strength of 0.2 to 1.5 N. A method for forming the packaging unit is provided.

38 Claims, 8 Drawing Sheets

(51) Int. Cl.
  *B65B 11/00* (2006.01)
  *B65B 51/02* (2006.01)
  *B65B 61/06* (2006.01)
  *B65D 65/14* (2006.01)
  *A61F 13/15* (2006.01)

(52) U.S. Cl.
  CPC ...... *A61F 13/5514* (2013.01); *A61F 13/5515* (2013.01); *A61F 13/55135* (2013.01); *B65B 11/004* (2013.01); *B65B 51/02* (2013.01); *B65B 61/06* (2013.01); *B65D 65/14* (2013.01); *B65D 2575/586* (2013.01)

(56) References Cited

U.S. PATENT DOCUMENTS

| | | | |
|---|---|---|---|
| 3,957,569 A | 5/1976 | Freitag | |
| 4,058,426 A * | 11/1977 | Pasic | B65B 9/026 |
| | | | 156/212 |
| 4,192,448 A * | 3/1980 | Porth | B65D 27/14 |
| | | | 229/80 |
| 4,483,445 A * | 11/1984 | Lepisto | B65D 33/06 |
| | | | 383/203 |
| 4,555,022 A * | 11/1985 | Eagon | A61F 13/5514 |
| | | | 206/438 |
| 4,781,712 A * | 11/1988 | Barabino | A61F 13/5514 |
| | | | 604/385.201 |
| 4,917,675 A * | 4/1990 | Taylor | A61F 13/5514 |
| | | | 206/440 |
| 5,167,739 A | 12/1992 | Hutchinson et al. | |
| 5,238,178 A | 8/1993 | Hutchinson et al. | |
| 5,375,764 A | 12/1994 | Sauerwine | |
| H1454 H | 6/1995 | Cucuzza et al. | |
| 5,462,166 A | 10/1995 | Minton et al. | |
| 5,567,260 A | 10/1996 | McFall | |
| 5,569,230 A | 10/1996 | Fisher et al. | |
| 5,591,153 A | 1/1997 | Mattingly, III | |
| 5,598,970 A | 2/1997 | Mudry et al. | |
| 5,769,837 A | 6/1998 | Parr | |
| 5,792,131 A | 8/1998 | Mizutani | |
| 5,868,727 A | 2/1999 | Barr et al. | |
| 5,882,789 A * | 3/1999 | Jones | B32B 7/06 |
| | | | 428/34.8 |
| 6,003,760 A | 12/1999 | Abercrombie | |
| 6,015,934 A | 1/2000 | Lee et al. | |
| 6,039,242 A | 3/2000 | Tee | |
| 6,176,850 B1 | 1/2001 | Rosenfeld et al. | |
| 6,186,993 B1 | 2/2001 | Toyoshima et al. | |
| 6,203,512 B1 | 3/2001 | Farris et al. | |
| 6,234,229 B1 | 5/2001 | Tabuchi | |
| 6,322,106 B1 | 11/2001 | Mehta et al. | |
| 6,644,697 B1 * | 11/2003 | Schinella | B42D 15/00 |
| | | | 229/72 |
| 6,681,668 B1 * | 1/2004 | Smirle | B26F 3/12 |
| | | | 139/291 C |
| 7,083,079 B2 | 8/2006 | Bethke | |
| 7,708,727 B2 | 5/2010 | Woltman et al. | |
| 8,231,590 B2 | 7/2012 | Zander et al. | |
| 8,900,210 B2 | 12/2014 | Drevik et al. | |
| 9,155,668 B2 * | 10/2015 | Dahl | A61F 13/5514 |
| 9,545,344 B2 * | 1/2017 | Ekstedt | A61F 13/551 |
| 9,821,940 B2 * | 11/2017 | Ekstedt | B65D 75/20 |
| 9,834,355 B2 * | 12/2017 | Dahlqvist | A61F 13/5514 |
| 2003/0163109 A1 | 8/2003 | Ohba et al. | |
| 2003/0225390 A1 | 12/2003 | Vogt et al. | |
| 2003/0234069 A1 | 12/2003 | Coenen et al. | |
| 2004/0107676 A1 | 6/2004 | Murray | |
| 2005/0137553 A1 | 6/2005 | Bechyne et al. | |
| 2005/0198931 A1 | 9/2005 | Cesiro et al. | |
| 2006/0025739 A1 | 2/2006 | DiPalma et al. | |
| 2006/0137568 A1 | 6/2006 | MacDonald et al. | |
| 2006/0212015 A1 * | 9/2006 | Peele | A61F 13/5518 |
| | | | 604/385.13 |
| 2007/0038197 A1 * | 2/2007 | Camille Nijs | A61F 13/5514 |
| | | | 604/385.02 |
| 2007/0049891 A1 | 3/2007 | Clark, Jr. et al. | |
| 2007/0189644 A1 | 8/2007 | Murray | |
| 2008/0067803 A1 | 3/2008 | Tanigawa | |
| 2009/0082747 A1 | 3/2009 | Carlen et al. | |
| 2010/0175825 A1 | 7/2010 | Baldauf | |
| 2010/0298797 A1 | 11/2010 | Ehlenbach et al. | |
| 2011/0028933 A1 | 2/2011 | Fung et al. | |
| 2011/0034897 A1 | 2/2011 | Nomoto et al. | |
| 2012/0090071 A1 | 4/2012 | Umebayashi | |
| 2012/0283682 A1 | 11/2012 | Otsubo et al. | |
| 2013/0165888 A1 | 6/2013 | Kinoshita et al. | |
| 2013/0199956 A1 | 8/2013 | Hunter et al. | |
| 2014/0155852 A1 | 6/2014 | Nishimura et al. | |
| 2015/0004367 A1 * | 1/2015 | Xu | A61F 13/15723 |
| | | | 428/171 |
| 2015/0112294 A1 | 4/2015 | Dahl et al. | |
| 2016/0228309 A1 * | 8/2016 | Ekstedt | A61F 13/551 |
| 2016/0242971 A1 * | 8/2016 | Ekstedt | A61F 13/551 |
| 2017/0151105 A1 * | 6/2017 | Holmberg | A61F 13/55135 |
| 2017/0151106 A1 * | 6/2017 | Dahlqvist | A61F 13/5514 |

FOREIGN PATENT DOCUMENTS

| | | |
|---|---|---|
| EP | 0 955 243 A2 | 11/1999 |
| EP | 2 589 356 A1 | 5/2013 |
| EP | 2 737 886 A1 | 6/2014 |
| GB | 2 273 279 A | 6/1994 |
| JP | H09-322909 A | 12/1997 |
| JP | 2000-51272 A | 2/2000 |
| JP | 2003-199786 A | 7/2003 |
| JP | 2006-45417 A | 2/2006 |
| JP | 2009-73498 A | 4/2009 |
| JP | 2013-85818 A | 5/2013 |
| JP | 2015-514542 A | 5/2015 |
| WO | WO 88/10219 A1 | 12/1988 |
| WO | WO 89/00459 A1 | 1/1989 |
| WO | WO 95/00092 A1 | 1/1995 |
| WO | WO 97/34556 A2 | 9/1997 |
| WO | WO 00/45767 A1 | 8/2000 |
| WO | WO 03/030796 A1 | 4/2003 |
| WO | WO 2005/087167 A1 | 9/2005 |
| WO | WO 2010/071512 A1 | 6/2010 |
| WO | WO 2010/135566 A1 | 11/2010 |
| WO | WO 2012/102071 A1 | 8/2012 |
| WO | WO 2012/157621 A1 | 11/2012 |
| WO | WO 2013/162430 A1 | 10/2013 |
| WO | WO 2014/188239 A1 | 11/2014 |

OTHER PUBLICATIONS

The extended European Search Report dated Oct. 16, 2017, by the European Patent Office in European Patent Application No. 14894531.4-1308. (7 pages).
Office Action (Examination Report No. 1 for Standard Patent Application) dated Feb. 13, 2017, by the Australian Patent Office in corresponding Australian Patent Application No. 2014396900. (3 pages).
Ciba-Geigy AG (Durr's) Applications [1977] RPC 83. Published Feb. 17, 1977.
Section 2.9.2.8 of Australian Patent Manual of Practice & Procedure, titled "Printed Matter". Retrieved Feb. 19, 2017. <http://manuals.ipaustralia.gov.au/patents/national/patentable/2.9.2.8_printed_matter.htm>. (2 pages).
Wikipedia, "Corona treatment", http://en.wikipedia.org/wiki/Corona_treatment, Mar. 16, 2015, 6 pages.
International Search Report (PCT/ISA/210) dated Feb. 23, 2015, by the Swedish Patent Office as the International Searching Authority for International Application No. PCT/SE2014/050724.
Written Opinion (PCT/ISA/237) dated Feb. 23, 2015, by the Swedish Patent Office as the International Searching Authority for International Application No. PCT/SE2014/050724.
International Preliminary Report on Patentability (PCT/IPEA/409) dated Jun. 8, 2016, by the Swedish Patent Office as the International Searching Authority for International Application No. PCT/SE2014/050724.

(56) References Cited

OTHER PUBLICATIONS

International Search Report (PCT/ISA/210) dated Feb. 20, 2015, by the Swedish Patent Office as the International Searching Authority for International Application No. PCT/SE2014/050725.
Written Opinion (PCT/ISA/237) dated Feb. 20, 2015, by the Swedish Patent Office as the International Searching Authority for International Application No. PCT/SE2014/050725.
International Preliminary Report on Patentability (PCT/IPEA/409) dated Jun. 13, 2016, by the Swedish Patent Office as the International Searching Authority for International Application No. PCT/SE2014/050725.
International Search Report (PCT/ISA/210) dated Feb. 16, 2015, by the Swedish Patent Office as the International Searching Authority for International Application No. PCT/SE2014/050719.
Written Opinion (PCT/ISA/237) dated Feb. 16, 2015, by the Swedish Patent Office as the International Searching Authority for International Application No. PCT/SE2014/050719.
International Preliminary Report on Patentability (PCT/IPEA/409) dated Jun. 14, 2016, by the Swedish Patent Office as the International Searching Authority for International Application No. PCT/SE2014/050719.
European Patent Office Letter dated Mar. 27, 2015, for International Application No. PCT/SE2014/050719.
International Search Report (PCT/ISA/210) dated Feb. 11, 2015, by the Swedish Patent Office as the International Searching Authority for International Application No. PCT/SE2014/050720.
Written Opinion (PCT/ISA/237) dated Feb. 11, 2015, by the Swedish Patent Office as the International Searching Authority for International Application No. PCT/SE2014/050720.
Written Opinion of the International Preliminary Examining Authority (PCT/IPEA/408) dated Jun. 3, 2016, by the Swedish Patent Office as the International Searching Authority for International Application No. PCT/SE2014/050720.
Written Opinion of the International Preliminary Examining Authority (PCT/IPEA/408) dated Jul. 7, 2016, by the Swedish Patent Office as the International Searching Authority for International Application No. PCT/SE2014/050720.
European Patent Office Letter dated Aug. 24, 2015, for International Application No. PCT/SE2014/050720.
European Patent Office Letter dated Jun. 29, 2016, for International Application No. PCT/SE2014/050720.
International Search Report (PCT/ISA/210) dated Mar. 2, 2015, by the Swedish Patent Office as the International Searching Authority for International Application No. PCT/SE2014/050726.
Written Opinion (PCT/ISA/237) dated Mar. 2, 2015, by the Swedish Patent Office as the International Searching Authority for International Application No. PCT/SE2014/050726.
Written Opinion of the International Preliminary Examining Authority (PCT/IPEA/408) dated Jun. 3, 2016, by the Swedish Patent Office as the International Searching Authority for International Application No. PCT/SE2014/050726.
International Preliminary Report on Patentability (PCT/IPEA/409) dated Jul. 12, 2016, by the Swedish Patent Office as the International Searching Authority for International Application No. PCT/SE2014/050726.
European Patent Office Letter dated Apr. 7, 2015, for International Application No. PCT/SE2014/050726.
International Search Report (PCT/ISA/210) dated Feb. 11, 2015, by the Swedish Patent Office as the International Searching Authority for International Application No. PCT/SE2014/050718.
International Preliminary Report on Patentability (PCT/IPEA/409) dated Jun. 8, 2016, by the Swedish Patent Office as the International Searching Authority for International Application No. PCT/SE2014/050718.
European Patent Office Letter dated Mar. 27, 2015, for International Application No. PCT/SE2014/050718.
English Translation of Office Action (Decision to Grant) dated Jan. 30, 2018, by the Russian Patent Office in Russian Patent Application No. 2017100892/12(001424). (9 pages).

* cited by examiner

Results of sealing strenght test

| Sample | Mechanical | | Embossed | | Adhesive | |
|---|---|---|---|---|---|---|
| | Max Load (N) | Work (Nmm/10mm) | Max Load (N) | Work (Nmm/10mm) | Max Load (N) | Work (Nmm/10mm) |
| 1 | 1,05 | 0,69 | 0,85 | 3,94 | 0,76 | 5,25 |
| 2 | 0,82 | 0,62 | 0,88 | 3,99 | 0,54 | 3,69 |
| 3 | 0,65 | 0,42 | 0,98 | 3,77 | 0,61 | 4,65 |
| 4 | 0,31 | 0,23 | 1,08 | 3,21 | 0,56 | 3,70 |
| 5 | 0,95 | 0,75 | 1,20 | 6,57 | 0,55 | 4,16 |
| 6 | 0,61 | 0,45 | 1,00 | 3,51 | 0,50 | 4,44 |
| 7 | 0,46 | 0,23 | 1,35 | 5,95 | 0,54 | 5,24 |
| 8 | 0,57 | 0,40 | 0,94 | 4,34 | 0,58 | 4,67 |
| 9 | 0,62 | 0,36 | 0,89 | 5,61 | 0,67 | 3,58 |
| 10 | 0,80 | 0,65 | 1,29 | 6,58 | 0,46 | 4,20 |
| Average | 0,68 | 0,48 | 1,04 | 4,75 | 0,58 | 4,36 |

*Fig.10*

PACKAGING UNIT FOR HYGIENE ARTICLES AND A METHOD OF FORMING A PACKAGING UNIT

TECHNICAL FIELD

The present disclosure relates to a packaging unit for hygiene articles. The present disclosure also relates to a method of forming a packaging unit for hygiene articles from a sheet of material.

BACKGROUND

Disposable hygiene articles, such as sanitary napkins and panty liners, are normally packaged individually in, for example, an easy wrap or a single wrap. Individual packages facilitate hygienic carrying of single articles for future use, e.g. in a handbag. The edges of the individual packages can sealed by means such as ultrasonic welding or heat welding. Further, the packaging units are often used both as a means for packaging an unused article and for disposal of the used article.

It is desirable that used articles of this kind can be disposed of discretely and hygienically. This may be particularly important when the user lacks the possibility to dispose of the used article immediately after the used article has been replaced, e.g. when there is no waste bin available in the toilet area. In this case, the user may need to put the used article in e.g. a handbag or backpack, which requires that the package is adequately sealed in order to avoid staining and odour.

To solve the problem of providing a single wrap that may be both used for packaging of a new and unused hygiene article and for safe and hygienic disposal of used hygiene articles, the use of "POST-IT-like" adhesives (low-tack, reusable, pressure-sensitive adhesive) has been shown to be useful as sealing means for the individual wrap packages.

WO2013/162430 A1 discloses such a packaging unit in the form a single wrap that can be used both for packaging of a new and unused hygiene article and for safe and hygienic disposing of used hygiene articles. The packaging unit is in the form of a sheet provided with adhesive in a certain chessboard pattern for closing and sealing the packaging unit. Such a sheet may be fabricated by providing a blank of sheet material on which, for example, adhesive is applied and cutting the web into individual sheets of material for forming the packaging unit.

Although the prior art packaging unit to some extent may alleviate the problems of providing a safe and hygienic packaging for unused as well as used hygiene articles, there is still a problem of providing adequate closure and sealing of the package by the use of adhesive, wherein the packaging unit may be undesirably opened and may have loose flanking edges and/or corners making the packaging unit unattractive to look at and to manipulate. It has also been shown that the manufacturing process of a packaging unit described in WO 2013/162430 may be adversely affected by the presence of adhesive on the packaging unit. For instance, during the folding step, the adhesive arranged at the edge portions of the packaging unit may be caught by the folding tool, which will either cause a transfer of the adhesive from the packaging unit to the tool, or will lead to an inaccurate folding. In both cases, manufacturing of the packaging unit will be impaired.

Thus, there is still a need for further improvements of packaging units so as to provide a packaging unit that is easy to produce as well as reliable to use and aesthetically appealing.

SUMMARY

In view of known packaging units, it is an object to provide an improved packaging unit arrangement for carrying new hygiene articles as well as used hygiene articles, which arrangement provides a packaging unit that is easy and reliable to produce, as well as being reliable to use, while being aesthetically appealing.

This object is wholly or partially achieved by a packaging unit according to appended claim 1 and a method according to appended claim 24. Embodiments are set forth in the appended dependent claims, in the following description and in the drawings.

Thus, there is provided a packaging unit for hygiene articles, the unit being formed from a sheet of material, the sheet having an inner surface and an outer surface. The inner surface comprises an edge zone comprising an inner edge portion and an outer edge portion, wherein at least one of the outer edge portion and the inner edge portion comprises at least one region being provided with a resealable adhesive for closure and sealing of the packaging unit, thus forming an adhesive zone. The sheet has at least one folding axis, the folding axis dividing the sheet into a first region and a second region, wherein the sheet is folded about the at least one folding axis with the first and second regions in an overlapping configuration, thereby providing a packaging unit of overlapping sheet layers. The overlapping outer edge portions of the sheet layers are at least partly adhesive-free and are at least partially connected to each other by a mechanical interaction providing a sealing strength of 0.2 to 1.5 N as measured according to the test method as described herein.

The packaging unit is in the form of a sheet that may be used as a single wrap that has resealable adhesive for closure of the packaging unit holding an unused a hygiene article therein or a used article therein.

By "sealing strength" is meant a maximum force in N of a connection between two layers as tested according to method described under the Example section herein.

As used herein, the term "inner surface" refers to the surface of the packaging unit facing the product positioned inside the packaging unit, and the term "outer surface" refers to the surface opposite to the inner surface, i.e. the surface facing the ambient.

By the term "edge zone" is meant the portion of the packaging unit adjacent to the edges of the packaging unit. The width of an edge zone may be varied. The edge zone may be divided into an inner edge portion and an outer edge portion. The term "inner edge portion" then refers to the portion of the edge zone positioned towards the center of the packaging unit, such as towards the longitudinal center line of the packaging unit. The term "outer edge portion" refers to the portion of the edge zone positioned towards the edge of the packaging unit.

By a "resealable adhesive" as used herein is meant an adhesive that ensures that an object may be attached to a surface using such an adhesive and subsequently detached from that surface, causing minor or no disruptions to the object or the surface. Furthermore, an object that has been peeled off may also be reattached to a surface again.

By "mechanical interaction" is here meant interaction that provides a connection between layers that does not require any adhesive for adequate connection. The connection by such a mechanical interaction may be provided by a cutting tool during formation of a folded packaging unit from a folded blank of elongated sheet material. The blank is then cut at the overlapping outer edge regions of two packing units to be formed as described further herein. It has been found that slight heating and tensioning of the sheet and layers occur during the manufacturing so that a cutting tool, such as a cutting roller with knives, mechanically joins and/or welds the cut layers together, thus providing a non-adhesive connection between the layers. The heat is generated by, for example, friction between the blank and manufacturing tools such as rollers. This serves to generate a slightly heated material that is cut by the cutting tool, something that also generates heat due to its weight and cutting speed. The cut layers therefore become joined and/or welded together. Preferably, the cutting is provided by a cutting tool that cuts the sheet in an axe-like manner, i.e. cuts the sheet as a stroke by an axe. The cutting roller exemplified herein provides such an axe-like cutting action.

The connection by mechanical interaction requires no weld or other sealing method other than the use of the cutting tool for sealing of the outer edge, even though it is preferred to combine such a connection with the resealable adhesive connection for closure of the packaging unit.

The mechanical interaction is not an embossed interaction. A connection by embossment is generally provided by rolling layers of sheet material between two rollers having surfaces provided with a "broad" pattern. The layers of sheet material are pressed together under high pressure by the rollers and by heating the materials. An embossed joint normally has a width of 2 to 10 mm.

To the contrary, the connection by the mechanical interaction according to the present disclosure may provide an elongated joint with a width of 0.05 to 0.5 mm, preferably, 0.1 to 0.2 mm.

It is the outer edge of the overlapping edge portions, in particular adhesive-free edge portions and/or folded packaging unit corners, that may benefit from becoming connected and sealed by the mechanical interaction. It has been found that the connection by mechanical interaction as, for example, provided by the cutting tool provides an adequate sealing of the outer edge portions, in particular adhesive-free outer edge portions, so as to provide a packaging unit without any loose flanking edges and/or corners. Furthermore, the connection ensures that corners of the folded packaging unit and its outer layer ("lid") are kept in an adequate and flat position during stacking and packing into bags or the like. The packaging unit also looks more attractive by not having any loose flanking edges and/or corners. A partial opening of the packaging unit and gluing to other units or items may also be prevented by the provision of the connection by the mechanical interaction.

The adhesive-free edge portions, together with the connection by the mechanical interaction, also lead to less manufacturing problems, as there is provided more space for the folding tool, while still providing a possibility of forming a sufficiently tightly sealed package around both a new and a used article.

Thus, in addition to the resealable adhesive, the connection by the mechanical interaction provides a hygienic packaging unit that is sufficiently tightly sealed around both a new and a used article.

The rather "weak" nature of the connection provided by the mechanical interaction provides less risk of disrupting the material during the opening of the packaging unit and thus also provides a reliable packaging unit for used products. The sealing strength of the connection may be comparable with a resealable adhesive connection, but lower than an embossed connection.

The sealing strength may be 0.2 to 1.1 N or 0.3 to 1 N.

The work required for separating the sheet layers connected to each other by the mechanical interaction may be 0.2 to 0.8 Nmm/10 mm as measured according to the test method as described in the specification. The work may be 0.3 to 0.7 Nmm/10 mm.

One of the inner edge portion and the outer edge portion of the edge zone of the first region may be provided with the resealable adhesive that forms a first adhesive zone, with the other of the inner edge portion and the outer edge portion of the edge zone of the first region being adhesive-free. The inner edge portion or the outer edge portion of the edge zone of the second region corresponding to the adhesive-carrying edge portion of the first region is adhesive-free, such that when the sheet is folded about the first folding axis, the edge portions carrying resealable adhesive in the first region are brought in contact with the adhesive-free edge portions in the second region.

A distance between the at least one first folding axis and the first adhesive zone may be 1-20 mm, preferably 2-18 mm, more preferably 3-15 mm.

Providing such a distance between the first folding axis and the first adhesive zone creates an adhesive-free portion between the first folding axis and the first adhesive zone. Thus, a folding tool may be positioned at the first folding axis without the risk of being caught by the resealable adhesive arranged at the first adhesive zone.

The distance between the first folding axis and the first adhesive zone may be varied depending on the dimensions of the packaging unit, and the size of the edge zones. Also, the distance between the first folding axis and the first adhesive zone should be optimized such that it provides sufficient space for the folding tool, wherein the mechanical interaction provides a possibility of forming a sufficiently tightly sealed package around both a new and a used article.

One of the inner edge portion and the outer edge portion of the edge zone of the second region complementary to the adhesive-carrying edge portion of the first region may be provided with resealable adhesive, thus forming a second adhesive zone. In such an embodiment, when the packaging unit is folded about the first folding axis, the edge portions carrying resealable adhesive in the first region are brought in contact with the adhesive-free edge portions in the second region, and the edge portions carrying resealable adhesive in the second region are brought in contact with the adhesive-free edge portions in the first region.

If the distance between the first folding axis and the first adhesive zone is sufficiently large to allow a folding tool to be positioned at the first folding axis without the risk of the folding tool being caught by the resealable adhesive of the second adhesive zone, the longitudinal extension of the second adhesive zone may be equal to the longitudinal extension of the second region. Preferably, the distance between the first folding axis and the second adhesive zone is 1-20 mm, preferably 2-18 mm, more preferably 3-15 mm, such that a space for positioning a folding tool is created on either side of the first folding axis. The distance between the first folding axis and the first adhesive zone and the distance between the first folding axis and the second adhesive zone may be the same or different.

The sheet of material may have a longitudinal direction (L) and a transverse direction (T) and be of a substantially rectangular shape and comprise longitudinal edges and transverse edges and sheet corner portions. The at least one folding axis may be at least one transversely extending folding axis, and the edge zones may be arranged along the longitudinal edges (L).

At least one of the corner portions may be free from resealable adhesive.

Providing such an adhesive-free corner minimize the risk of a manufacturing tool, such as a folding tool or cutting tool, becoming glued to the sheet of material and thus impairing the manufacturing process tool. A longitudinal extension and/or the transversal extension of the adhesive-free corners may be 1 to 3 cm.

The folded packaging unit of the overlapping sheet layers may have corner portions that are free from resealable adhesive.

As discussed above, the mechanical interaction provides a possibility of forming a sufficiently tightly sealed package around a new article, wherein the corner portions free from any adhesive may be tightly sealed, while there is provided less risk of impairing the manufacturing process of the packaging unit. The packaging unit may be formed without any loose corners. Furthermore, the connection means that corners of the folded packaging unit and its outer layer ("lid") are kept in an adequate and flat position during stacking and packing into bags or the like.

The sheet of material may comprise a first and a second transverse edge zone and at least a portion of at least one of the first and the second transverse edge zones may be provided with resealable adhesive. Preferably, the transverse edge zone of one of the first or the third regions is provided with resealable adhesive. In such an embodiment, folding should be initiated around the folding axis being adjacent to the region of the packaging unit comprising the adhesive-free transverse edge zone, such that the inner surface of the region comprising the adhesive-carrying transverse edge zone is brought into contact with the outer surface of the region comprising the adhesive-free transverse edge zone, thus forming additional means for providing a sufficiently tightly sealed package.

As mentioned above, the packaging unit comprises at least one first folding axis. The number of folding axes may vary depending on how the packaging unit is intended to be folded. It is preferred that the packaging unit comprises between one and three folding axes.

The sheet may have two folding axes, dividing the sheet into the first region, the second region and a third region, the sheet being folded along the folding axes with the first, second and third regions in an overlapping configuration of three layers, wherein outer edge portions of the three layers are at least partly connected to each other by the mechanical interaction.

One of the inner and outer edge portions of the edge zone of the third region may be provided with resealable adhesive, thus forming a third adhesive zone. A distance between the second folding axis and the third adhesive zone may be 1-20 mm, preferably 2-18 mm, more preferably 3-15 mm.

The sheet may have a first and a second folding axis dividing the sheet into the first region, the second region and the third region. If the edge portion and the outer edge portion of the edge zone of the second region are provided with resealable adhesive, the inner edge portion and the outer edge portion of the edge zone of the third region may be adhesive-free.

The sheet may be a single-ply material. The single-ply material may be of polyolefin that may comprise or be of polyethylene and/or polypropylene. The material of polyethylene and/or polypropylene may have a basis weight of 14 to 30 g/m$^2$.

The packaging unit may comprise one or more sync marks for indication of a positioning of the sheet of material during manufacturing of the packaging unit.

By the term "sync mark" is meant a position mark for synchronizing a positioning of the packaging unit and its parts during manufacturing thereof. The sync mark may be provided on the sheet and used as a mark for discerning the individual packing unit and regions thereof during production thereof. For example, it may be used as a positioning mark for indicating a cutting position of a blank sheet of material for providing a single packaging unit such as a wrap. Also, the sync mark may be used as a mark for determining whether, for example, the resealable adhesive is applied at a predetermined position on the packaging unit.

The sync mark may be a printed mark. The printed mark may be provided by a contact printing technique such as flexographic printing, rotogravure printing, screen printing and offset printing. The printed mark may also be provided by a non-contact printing technique, such as ink jet printing, wax jet printing, bubble jet printing and laser jet printing.

The resealable adhesive may be a pressure-sensitive hot-melt adhesive. Such an adhesive provides unlimited open time, meaning that the adhesive can bond to another substrate at any time. It is may provide "POST-IT-like" adhesive properties (low-tack, reusable, pressure-sensitive adhesive properties). Thus, the packaging unit may be reclosable.

Accordingly, the pressure-sensitive adhesive used with the packaging unit is one which has a very high self-adhesion but which can be readily separated or released from other materials, such as plastic materials or paper which has been treated with a release agent. A major advantage of the packaging unit according to the present disclosure is that it can be completely unfolded when a new hygiene article is about to be taken out. In contrast thereto, prior art packages having adhesively sealed edges with adhesive-coated edge portions in contact with each other have too high adhesive strength of the adhesively sealed edges, and any attempt to completely unfold the package generally leads to tearing and breakage of the packaging unit, making it unusable for discrete and hygienic disposal of the used article. As the adhesive-coated edge portions of the packaging unit of the present disclosure are not in contact with each other when the packaging unit is folded, the packaging unit can be readily opened and resealed, providing a tight disposal package. At the same time, the tensile strength of the adhesively sealed edges of the packaging unit using the resealable adhesive pattern of the present disclosure is sufficient to provide a tight package for both a new and a used article, and low enough to provide a readily-opened package.

The resealable adhesive used in the present disclosure may be a pressure-sensitive hotmelt adhesive, such as Lunatack® D656 BD 19 available from H. B. Fuller.

The length of the adhesive-covered edge portions in each region may be equal to or shorter than the length or width of each region. The width of the adhesive-covered edge portions may be varied depending on the adhesive strength desired. The wider the adhesive-covered edge zones, the stronger the sealing. The width of the adhesive-covered edge portions may be same or different in the different regions.

The sheet of material forming a packaging unit according to the present disclosure may comprise an odour-inhibiting or odour-neutralising substance. Such a substance may be applied in any suitable manner known to the person skilled in the art, e.g. as a coating, activatable microcapsules, impregnated patches, or the like.

It is conceivable that the sheet for forming a packaging unit according to the present disclosure may be stretchable or expandable, which may be advantageous if the hygiene article is greatly deformed during use, and may thus be difficult to wrap without deforming the packaging unit.

It should be noted that when the packaging unit according to the present disclosure is used for disposal, the user may choose to roll up the packaging unit instead of folding it, regardless of the resealable adhesive pattern at the edge zone of the packaging unit.

The inner surface may comprise a center zone that comprises a portion provided with a release agent.

The term "central zone" refers to the portion of the packaging unit excluding the edge zone and overlapping with the center of the packaging unit.

The release agent is intended for releasable connection to an adhesive of a hygiene article in the packaging unit. The release agent may be a silicone polymer or polysiloxane.

As an alternative, a release liner may be attached to the central zone of the inner surface.

Such a release liner is also intended for releasable connection to a hygiene article. The release liner may be manufactured from any suitable material known to the person skilled in the art, such as paper, non-woven or plastic film material. Further, in order to provide a release liner that is easily detachable from the garment-affixing adhesive that may be present on a garment-facing surface of the hygiene article, the release liner may be silicone-coated on the surface of the release liner that is intended to be connected to the hygiene article. The hygiene article may be releasably affixed to the release liner either by means of a resealable adhesive or by any other suitable fastening means known to the person skilled in the art, e.g. hook-and-loop fastening means.

"Releasably affixed" means two surfaces being bonded to each other such that the bond may be readily broken without affecting the surfaces.

The packaging unit may comprise a hygiene article.

There is also provided a method of forming a packaging unit for hygiene articles. The unit is formed from a blank of an elongated sheet of material. The method comprising the steps of:
 providing the elongated sheet of material comprising at least two packaging unit sections for forming two packaging units, the elongated sheet having first and second surfaces, the first surface comprising an inner surface of each packaging unit and the second surface comprising an outer surface of each packaging unit, wherein the elongated sheet comprises at least one folding axis extending in the machine direction (MD), the folding axis dividing the elongated sheet into a first blank region and a second blank region,
 applying a resealable adhesive on an edge zone portion of the inner surface of each packaging unit section;
 folding the elongated sheet along the at least one folding axis with the first and second blank regions in an overlapping configuration to provide a folded blank of overlapping sheet layers, and
 cutting the folded blank into two or more single packaging units by a use of a cutting and sealing tool.

Each formed packaging unit comprises the inner and outer surfaces, an inner edge portion and an outer edge portion, wherein at least one of the outer edge portion and the inner edge portion comprises at least one region being provided with the resealable adhesive forming an adhesive zone, the resealable adhesive being provided for closure and sealing of the packaging unit, wherein overlapping outer edge portions of sheet layers of the packaging unit are at least partly adhesive-free and are at least partially connected to each other by a mechanical interaction providing a sealing strength of 0.2 to 1.5 N as measured according to the test method as described herein.

The transversely extending folding axis extends along the machine direction (MD) and the cutting may occur along the cross machine direction (CD).

The method may, prior to the folding step, comprise:
 applying a release agent on the first surface on a portion of each center zone of a packaging unit section,
 applying a resealable adhesive on the portion with release agent, and
 applying a hygiene article to the adhesive applied on the release agent.

The method may, prior to the folding step, comprise:
 attaching a release liner on the first surface on a portion of each center zone of a packaging unit section and
 connecting a hygiene article to the release liner by the use of fastening means.

Thus, the hygiene article may be releasably affixed to a surface of the release liner after the release liner has been permanently attached to the inner surface of the packaging unit. Alternatively, the hygiene article may be releasably affixed to the user-facing surface of the release liner before the release liner has been permanently attached to the inner surface of the wrapping sheet. The hygiene article may be releasably affixed to the release liner either by means of a resealable adhesive or by any other suitable fastening means known to the person skilled in the art, e.g. hook-and-loop fastening means.

The method may further comprise providing the blank with one or more sync marks and detecting the sync mark and its position on the blank, wherein a position of cutting is determined based on a detected position of the sync mark. Each portion with adhesive that is arranged in an edge zone of a packaging unit section, and the position of the adhesive, may also be determined based on the position of the sync marks.

One or more sync mark detectors may be arranged to detect the sync mark the elongated sheet during the manufacturing, wherein a detection of the sync mark is used for indicating a position of a blank sheet of material so as to determine, for example, a cutting position of the blank sheet of material for providing single packaging unit such as a wrap.

The formed packaging unit for hygiene articles may be a packaging unit as defined above Thus, any chessboard-like pattern of resealable adhesive and non-adhesive portions as described herein above may be applied along the inner and outer edge portions of the edge zones for complementary attachment between resealable adhesive and non-adhesive portions in the formed folded packaging unit. This means that the resealable adhesive and the arrangement thereof on the inner surfaces of the first, second and third regions may be as described for the packaging unit above. There may be complementary resealable adhesive portions between the regions, and there may also be adhesive-free portions. Furthermore, the edge zones may be provided with one or more adhesive zones that are arranged at a distance from the at least one folding axis, so that a section of the edge zone about one folding axis is free of any adhesive for closure of the packaging unit.

Thus, the elongated sheet section may have a longitudinal direction (L) and a transverse direction (T) and be of a substantially rectangular shape and comprise longitudinal edges and transverse edges and sheet corner portions. At least one of the corner portions may be free from any adhesive for closure of the packaging unit.

The folded packaging unit of the overlapping sheet layers may have corner portions that are free from any adhesive for closure of the packaging unit.

The present disclosure will now be described in more detail with reference to embodiments and drawings.

BRIEF DESCRIPTION OF THE DRAWINGS

FIG. 10 is a table showing test results for sealing strengths and work for samples according to the present disclosure and comparative samples.

DETAILED DESCRIPTION OF EMBODIMENTS

The packaging unit according to the present disclosure is in the form of a sheet that may be used as a single wrap that has resealable adhesive for closure of the packaging unit holding an unused a hygiene article therein or a used article therein. The closure of the packaging unit may include folding the sheet and enclosing the hygiene article between folded sheet layers that are sealed by the resealable adhesive provided close to the edges of the sheets. Conceivable hygiene articles are sanitary napkins, panty liners and the like.

In the following, the packaging unit will be exemplified by a packaging unit comprising a rectangular sheet. Other forms may also be considered within the scope of the appended claims. Furthermore, the exemplified packaging unit comprises resealable adhesive for closure of the packaging unit, wherein a chessboard pattern of resealable adhesive and non-adhesive portions is formed along at least longitudinal edge zones (i.e. along the longitudinal direction (L)) for complementary attachment between resealable adhesive and non-adhesive portions in a folded packaging unit. According to the present disclosure, other ways of applying one or more resealable adhesive portions for closure of the packaging unit may also be considered.

Figure 1:
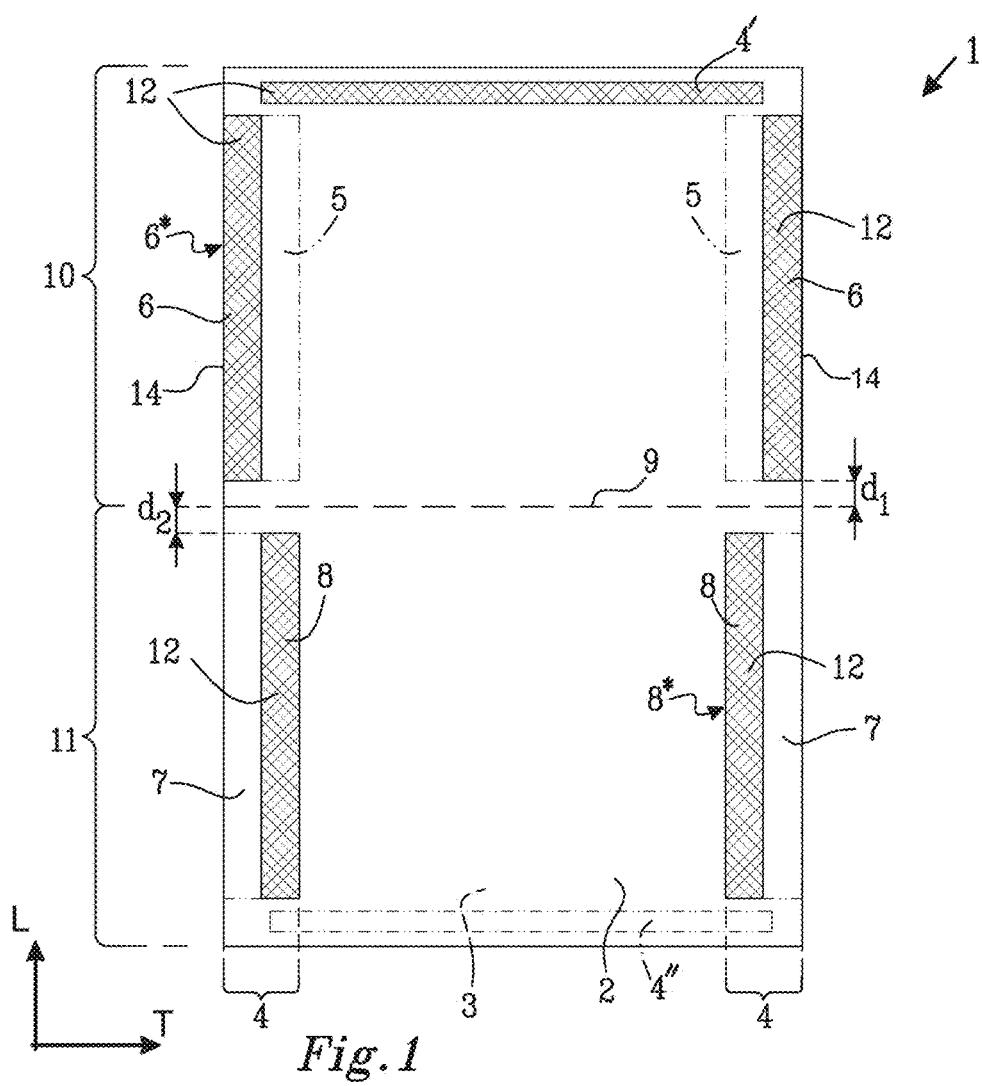
FIG. 1 shows a packaging unit according to an embodiment having one folding axis.
Figure 2:
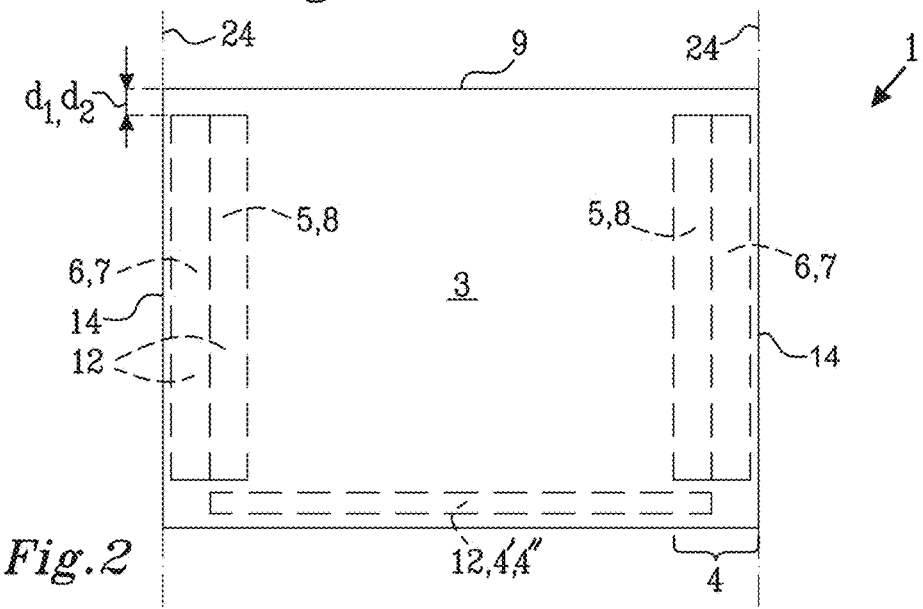
FIG. 2 shows the packaging unit depicted in FIG. 1 in a folded state.

FIG. 1 depicts a packaging unit 1 for hygiene articles according to an embodiment. The packaging unit is formed from a sheet of material having an inner surface 2 and an outer surface 3, the inner surface comprising an edge zone 4 comprising an inner edge portion 5, 8 and an outer edge portion 6, 7. The packaging unit 1 also comprises a first transverse edge zone 4' and a second transverse edge zone 4". The sheet has a first folding axis 9, wherein the folding axis divides the sheet into a first region 10 and a second region 11. As shown in FIG. 1, the outer edge portion 6 of the edge zone 4 of the first region 10 is provided with resealable adhesive 12, thus forming a first adhesive zone 6*, while the inner edge portion 5 of the edge zone 4 of the first region 10 is adhesive-free. As may be seen in FIG. 1, the first adhesive zone 6* is arranged at a distance $d_1$ from the first folding axis 9, to thereby provide a sufficient space for a folding tool to be positioned at the first folding axis 9. In the embodiment shown in FIG. 1, the distance $d_1$ is 5 mm. Further, the inner edge portion 8 of the edge zone 4 of the second region 11 is provided with resealable adhesive 12, thus forming a second adhesive zone 8*, while the outer edge portion 7 of the edge zone 4 of the second region 11 is adhesive-free. As depicted in FIG. 1, the second adhesive zone 8* is arranged at a distance $d_2$ from the first folding axis 9, the distance $d_2$ being 5 mm. Also, the first transverse edge zone 4' of the first region 10 is provided with resealable adhesive 12, while the second transverse edge zone 4" of the second region 11 is adhesive-free. Thus, the adhesive pattern in the first region 10 is complementary to the adhesive pattern of the second region 11. This, in turn, means that when the sheet is folded about the first folding axis 9, as shown in FIG. 2, the edge portions 6 carrying resealable adhesive 12 in the first region 10 are brought in contact with the adhesive-free edge portions 7 in the second region 11, the edge portions 8 carrying resealable adhesive 12 in the second region 11 are brought in contact with the adhesive-free edge portions 5 in the first region 10, and the first transverse edge zone 4' carrying resealable adhesive 12 in the first region 10 is brought in contact with the adhesive-free second transverse edge zone 4" in the second region 11. The space provided by the distances $d_1$ and $d_2$ at each side of the first folding axis 9 ensures facilitated and accurate folding.

The overlapping outer edge portions of the sheet layers as set forth in FIG. 2 are at least partly adhesive-free and are at least partially connected to each other by a mechanical interaction providing a sealing strength of 0.2 to 1.5 N as measured according to the test method as described herein. The mechanical interaction at least partly extends along the line 14 that represents a cutting line 14 that may be provided by a cutting tool during the formation of a folded packaging unit 1 from a folded blank of elongated sheet material that is cut at the overlapping outer edge regions of two packing units to be formed as described further herein.

Figure 3:
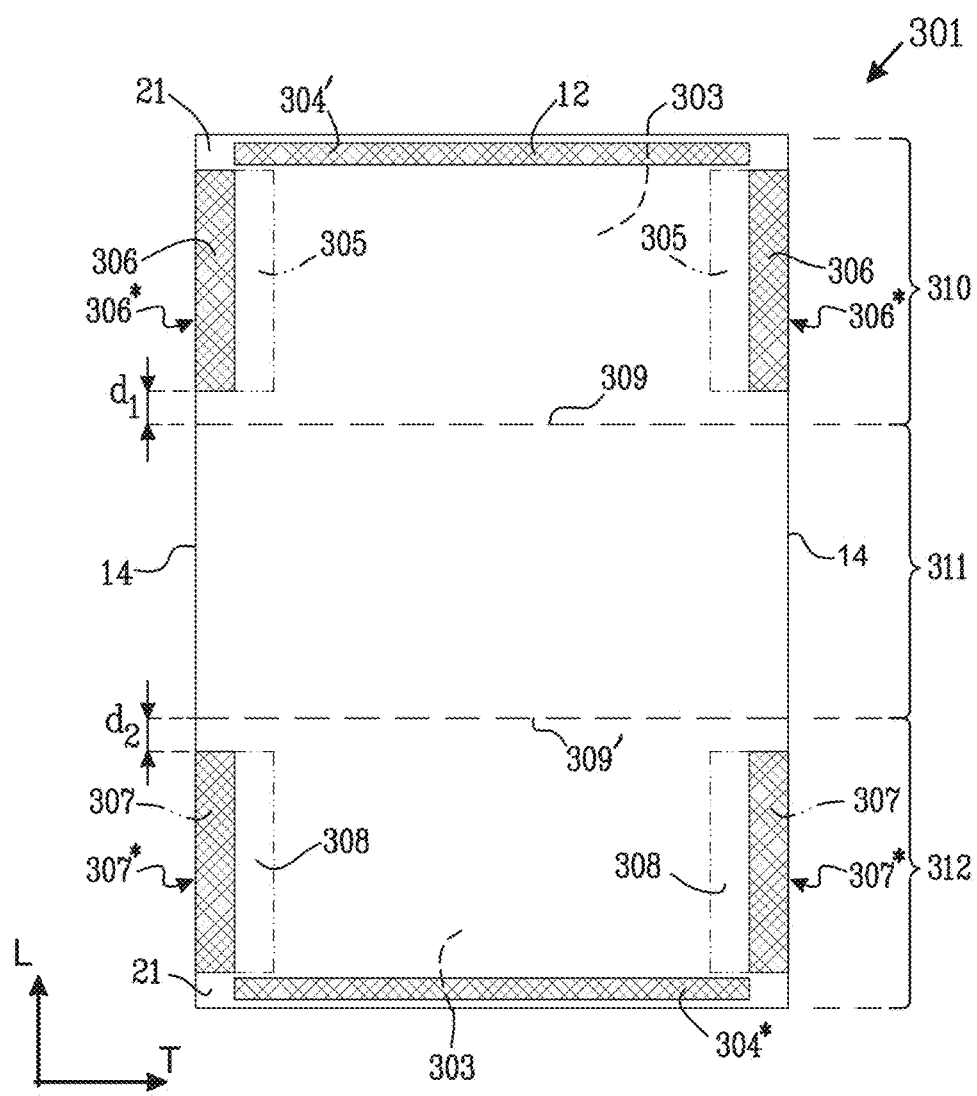
FIG. 3 shows a packaging unit according to an embodiment having two folding axes.
Figure 4:
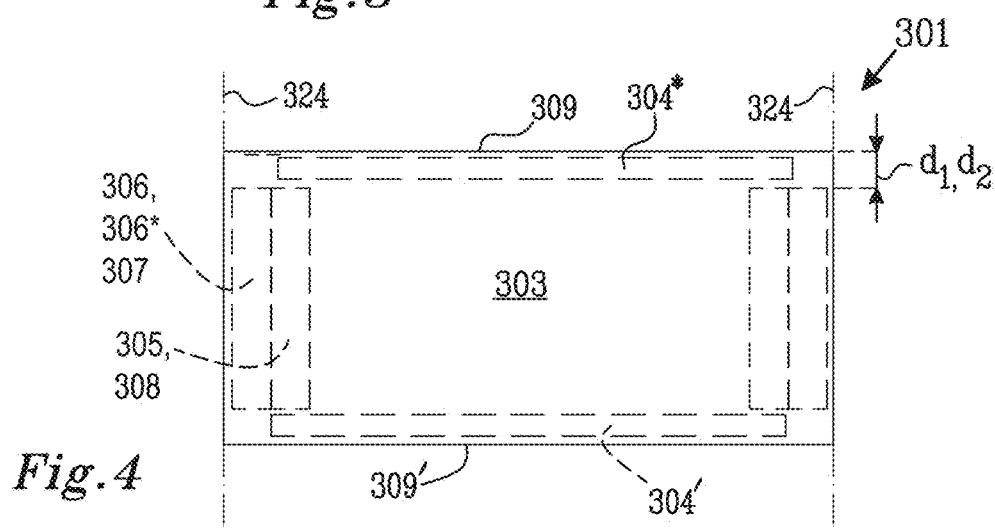
FIG. 4 shows the packaging unit depicted in FIG. 3 in a folded state.

The most common packaging unit for individual packaging of absorbent articles is a rectangular sheet comprising two folding axes, longitudinal edges and transverse edges. Such an embodiment is illustrated in FIG. 3. The packaging unit 301 is a rectangular sheet comprising a first folding axis 309 and a second folding axis 309' dividing the packaging unit into a first region 310, a second region 311 and a third region 312. Each of the regions comprises an inner edge portion 305, 308 and an outer edge portion 306, 307. As shown in FIG. 3, the outer edge portions 306, 307 of the first and third regions respectively are provided with resealable adhesive 12, thus forming a first 306* and a third adhesive zone 307*, respectively, while the inner edge portions 305, 308 of the first and third regions respectively are adhesive-free. As may be seen in FIG. 3, the first adhesive zone 306* is arranged at a distance $d_1$ from the first folding axis 309, thereby providing a sufficient space for a folding tool to be positioned at the first folding axis 309. In the embodiment shown in FIG. 3, the distance $d_1$ is 7 mm. Further, the third adhesive zone 307* is arranged at a distance $d_2$ from the second folding axis 309', the distance $d_2$ being 7 mm. Both the outer edge portion and the inner edge portion of the second region 311 are adhesive-free. This, in turn, means that when the sheet is e-folded about the folding axes 309, 309', as shown in FIG. 4, the outer edge portions 306 of the first region 310 or the outer edge portions 307 of the third region 312 carrying resealable adhesive 12 are brought in contact with the adhesive-free outer edge portions in the second region 311, depending on whether the folding is initiated around the first folding axis 309 or the second folding axis 309', and thus on which of the first and the third regions 310, 312 that is brought in contact with the second region 311. It should be noted that the order in which the packaging unit depicted in FIG. 4 is folded is irrelevant. For example, the packaging unit may be folded around the second folding axis 309', bringing the third region 312 in contact with the second region 311, sealing the outer edge portions 307. The packaging unit is subsequently folded around the first folding axis 309', bringing the first region 310 in contact with the outer surface of the third region 312, thus sealing the packaging unit (FIG. 4). The folding order may also be reversed. This is a great advantage, since when the packaging unit of the present disclosure is used for disposal, the user does not have to fold the packaging unit in any particular order to be able to obtain a tightly sealed package. The packaging unit will provide a sufficiently tight and hygienic package regardless of the folding order.

In order to obtain a tight package, the first and second transverse edge zones 304' and 304*  of the packaging unit 301 are provided with resealable adhesive 12. When both transverse edge zones 304' and 304*  are provided with resealable adhesive, the folding order is irrelevant, as described above. It is also conceivable to provide only one of the first and the second transverse edge zones 304' and 304*  with resealable adhesive. In this case, the folding is to be initiated around the folding axis being positioned closest to the adhesive-free transverse edge zone, such that the region comprising the adhesive-covered transverse edge zone forms a lid and the resealable adhesive positioned at the transverse edge zone seals the packaging unit.

The adhesive-covered portions are positioned such that at least one of the corner portions 21 of the packaging unit 301 is adhesive-free (FIG. 3). Thus, the overlapping outer edge portions of the sheet layers as shown in FIG. 4 are at least partly adhesive-free and are at least partially connected to each other by a mechanical interaction providing a sealing strength of 0.2 to 1.5 N as measured according to the test method as described herein.

The mechanical interaction at least partly extends along the line 324, that represents a cutting line 324 that may be provided by a cutting tool during the formation of a folded packaging unit from a folded blank of elongated sheet material that is cut at the overlapping outer edge regions of two packing units to be formed, as described further herein.

It should be noted that when the packaging unit according to the present disclosure is used for disposal, the user may choose to roll up the packaging unit 1, 301 with the soiled article positioned on it rather than folding it.

The packaging unit is intended to include a hygiene article. The hygiene article may be arranged on the inner surface, in the center zone thereof, wherein the hygiene article may be attached to a release agent via an adhesive or to a release liner (not shown), as now will be further elaborated on in the described example of a method of forming the packaging unit.

Figure 5:
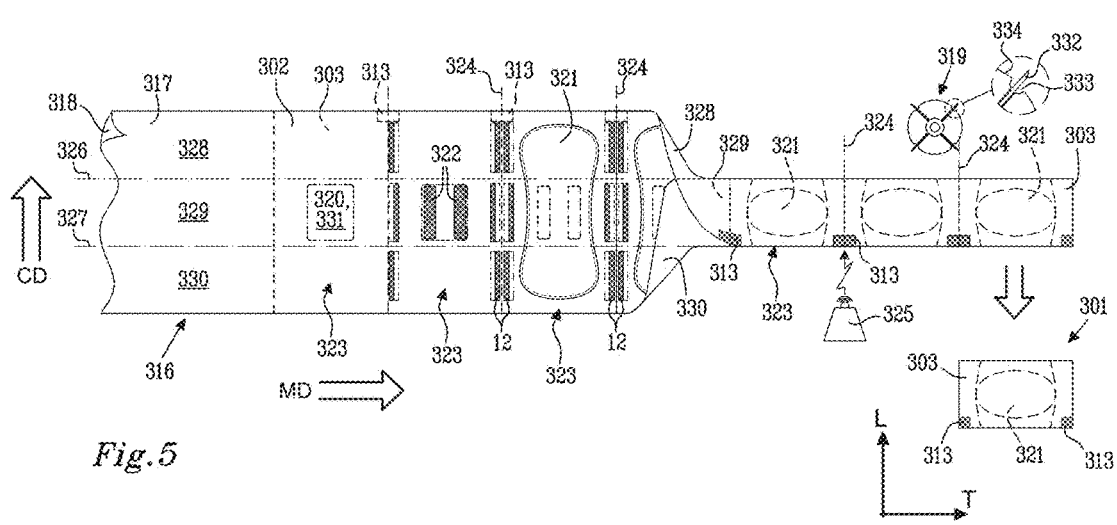
FIG. 5 schematically illustrates an arrangement for forming a packaging unit.

The packaging units may be formed from a blank. FIG. 5 schematically illustrates an arrangement of using a blank 316 for forming a packaging unit 301 with two folding axes 309, 309' in accordance with the packaging unit 301 shown in FIGS. 3 and 4. The blank 316 is an elongated sheet of material having first and second surfaces 317, 318, wherein the first surface comprises the inner surface 302 of each packaging unit 301 and the second surface 318 comprises the outer surface 303 of each packaging unit 301. The inner surface is provided with resealable adhesive 12 for closure of the packaging unit 301 formed from the blank 316, and the outer surface 303 is provided with one or more sync marks 313. Such a sync mark 313 may be used for guiding a cutting tool 319 to cut the blank 316 into individual sheets of material and forming the packaging units 301.

A release agent 320 or a release liner may be applied on the first surface 317 and inner surface 302, and a hygiene article 321 may be arranged on the release agent 320 via an adhesive 322 or on the release liner via fastening means.

The longitudinal edge zones of the packaging unit are at least partly adhesive-free and are at least partially connected to each other by a mechanical interaction 313, preferably partly or completely along the longitudinal edges as illustrated in FIG. 4. The width joint provided by the mechanical interaction may be 0.05 to 0.5 mm, preferably, 0.1 to 0.2 mm.

The method used in the arrangement as illustrated in FIG. 5 then comprises the steps of:
  providing a blank 316 of an elongated sheet of material comprising at least two packaging unit sections 323, the sheet having first and second surfaces 317, 318, the first surface 317 comprising an inner surface 302 of each packaging unit 301, and the second surface 318 comprising an outer surface 303 of each packaging unit 301,
  providing the outer surface 303 with one or more sync marks 313, e.g. one or more printed marks;
  applying a resealable adhesive 12 on an edge zone portion of the inner surface 302 of each packaging unit section 323;
  detecting the sync mark 313 and its position on the blank 316, and
  cutting the elongated sheet along a cutting line 324 into two or more packaging units 301.

The position of cutting and thus the cutting line may be determined based on the detected position of the sync mark (-s) 313.

In FIG. 5, each sync mark 313 is provided on the outer surface 303 of the sheet at a corner portion of the first region 310. Each sync mark 313 is applied on the blank as a combined sync mark overlapping the cutting line 324, and thus the combined sync mark forms two sync marks 313 after the blank 316 has been cut, wherein a sync mark 313 is formed on each packaging unit.

Each portion with resealable adhesive 12 may be arranged in a zone close to and along the cutting line 324 of a packaging unit section 323, wherein the resealable adhesive 12 in some portions may be applied as one resealable adhesive string along and overlapping the cutting line 323-324 so that the applied string forms a portion with resealable adhesive 12 on each one of two packaging units 301 after cutting has taken place (not shown). The resealable adhesive 12 may also be separately applied to each packaging unit section 323 at a distance from the cutting line 324.

One or more sync mark detectors may be arranged to detect sync marks on the outer surfaces 303 during the manufacturing, wherein detection of the sync marks is used for indicating a position of a blank 316 sheet of material so as to determine, for example, a cutting position of the blank sheet of material for providing single packaging unit such as a wrap. FIG. 5 illustrates one detector 325.

The elongated sheet may comprise at least one folding axis 326, 327 extending in the machine direction (MD). In FIG. 5, the elongated sheet has two folding axes 326, 327 dividing the elongated sheet into a first blank region 328, a second blank region 329 and a third blank region 330. The method illustrated in FIG. 5 further comprises folding the elongated sheet along the folding axes 326, 327 with the blank regions in an overlapping configuration, thereby providing a folded elongated sheet of overlapping sheet layers, wherein the step of cutting the elongated sheet occurs after the folding step. The transversely extending folding axes 326, 327 extend along the machine direction (MD) and the cutting occurs along the cross machine direction (CD). The folding is provided by any folding tool, as is well known in the art (not shown).

The cutting may be performed by a cutting roller 319 as illustrated in FIG. 5. The cutting roller 319 comprises a number of cutting blades 332 or knifes arranged along and at least partially within a recess 333 arranged on an outer surface 334 of the roller that is intended to be in contact with the folded blank 316 for cutting, the recess extending in a direction parallel to the rotation axis of the roller. The distance from the blade to the edge of the recess may be about 1.5 mm. The skilled person will appreciate, in view of the disclosure herein, which cutting speed, blank feeding speed, nip pressure applied by the cutting roller to the folded blank and other standard process conditions that are required to provide the requisite mechanical interaction.

Prior to the folding step, the method as illustrated in FIG. 5 further comprises:
applying a release agent 320 on the first surface 317 on a portion of each center zone 331 of a packaging unit section 323 (and corresponding packaging unit 301),
applying an adhesive 322 on the portion with release agent 320, and
applying a hygiene article 321 to the adhesive 322 applied on the release agent 320.

The sync mark (-s) 313 may also aid in positioning of the applied agents and articles.

As an alternative to using a release agent 320, and on the first surface 317 as illustrated in FIG. 5, the method may, prior to the folding step, further comprise:
attaching a release liner on the first surface 317 on a portion of each center zone 331 of a packaging unit section 323 and
connecting a hygiene article 321 to the release liner by the use of fastening means.

As the skilled person will appreciate, it is intended that the detailed description be regarded as illustrative and that many embodiments and alternatives are possible within the scope of the present disclosure as defined by the appended claims. For example, the packaging unit may adopt other shapes than the rectangular ones shown in the drawings. Furthermore, the present disclosure has been exemplified with packaging units comprising resealable adhesive for closure of the packaging unit, wherein a chessboard-like pattern of resealable adhesive and non-adhesive portions is formed along at least longitudinal edge zones (i.e. along the longitudinal direction (L)) for complementary attachments between resealable adhesive and non-adhesive portions in a folded packaging unit. Other ways of applying one or more resealable adhesive portions for closure of the packaging unit may also be considered.

EXAMPLES AND TEST METHOD

Aim and Samples

Figure 6:
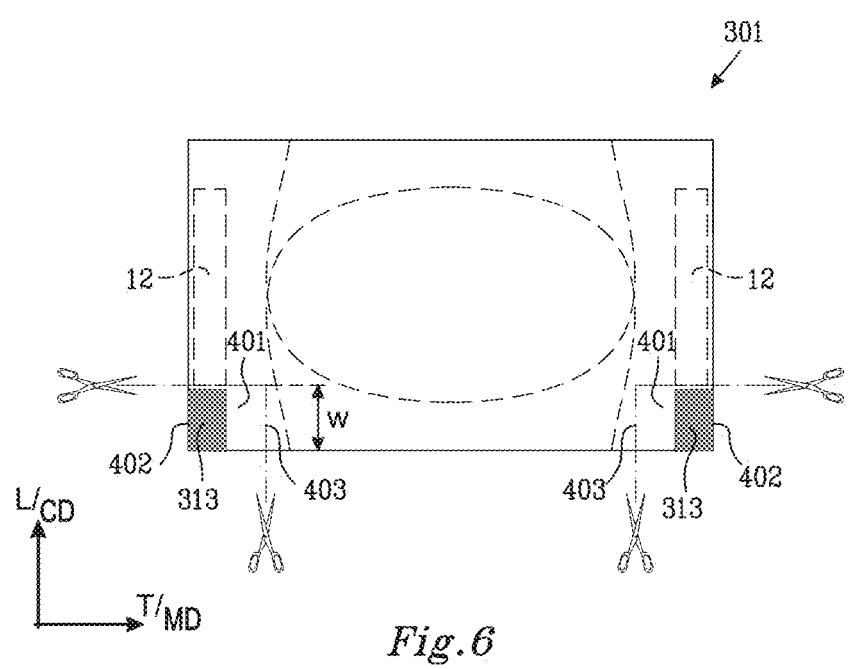
FIG. 6 shows how samples for testing the sealing strength and work are taken from a folded packaging unit.

The aim of the test method is to determine the sealing strength being the maximum force in a separation of a weld, and the connection between two layers of material, and to determine the work required to separate the layers from each other. This is done by using a tensile tester, wherein the test is performed in a crosswise direction compared to the normal opening direction in the longitudinal direction (L) of a packaging unit, when opening such packaging unit in the normal use of the product inside (FIG. 6). The tensile tester has a fixed bottom clamp, and a movable upper clamp. A suitable test apparatus and software are available from, for example, Instron Corporation or Lloyd Instruments.

FIG. 6 illustrates a packaging unit and how sample portions that are used are sliced out from the packaging unit for the tests. The samples 401 are taken from adhesive-free corners of the packaging unit, wherein one short side 402 of each sample includes a connection with mechanical interaction. The width (w) of each sample is 10 mm, also being the length of the short side 402 and the connection joint. The sample may be a two-layer or a three layer sample, depending on the type of packaging unit. The present samples are taken from packaging units 301 of the type that is illustrated in FIGS. 3 and 4, wherein the samples are of three layers. The packaging unit has been produced in a machine direction (MD), wherein the cutting of the samples provides a leading (front) sample in the MD and a trailing (back) sample in the MD, and both samples may be used in the test (FIG. 6).

Corresponding comparative samples with embossed connections and resealable adhesive connections were also prepared and tested.

The width of the tested mechanical interaction was about 0.1 mm. The embossed connection and the resealable adhesive connection had a width of about 4 mm.

Apparatus and Settings

Tensile tester

The pulling speed should be 300 mm/min

The pulling length should be 30 mm

The distance between upper and lower clamps should be adapted to the sample.

The width of tensile tester clamps should be wider than the sample width, i.e. more than 10 mm Scissor or punching tool.

Sample Preparation

Samples should be conditioned to 23 degrees C., 50% Relative Humidity for 24 hours before testing is performed.

Samples are cut by scissors or punched with a punching tool as illustrated in FIG. 6. It is important to cut out extra material in the separation direction (T) to be able to fit the sample in the tensile tester. If possible, any part of the hygiene article arranged inside the wrap should be removed. If necessary, any other sealing or connection means that will disturb the test of the connection of interest should also be removed. It should be noted that it has been shown that the provision of a sync mark 313 does not disturb a sample and a joint (connection) thereof to be tested Test Procedure The test was performed using a three-layer sample. Therefore, the free-end short-side edges 403 of two of the sample layers were inserted in the upper clamp and the short-side edge 403 of the remaining single layer material was inserted in the lower clamp. The sample should be handled gently so as not to interfere with the connection to be tested. The sample were and should be fitted in the center of the each clamp (sideways) and the connection to be tested and should be centered in the middle of the clamp opening between the clamps. The extension of the connection should be placed perpendicular to the pulling direction.

The test measurement with the tensile tester may then be started.

Results

The results are reported as the maximum force of the sealing in N using one decimal (sealing strength), and the performed work in Nmm/10 mm using whole numbers have been calculated.

Examples

Figure 7:
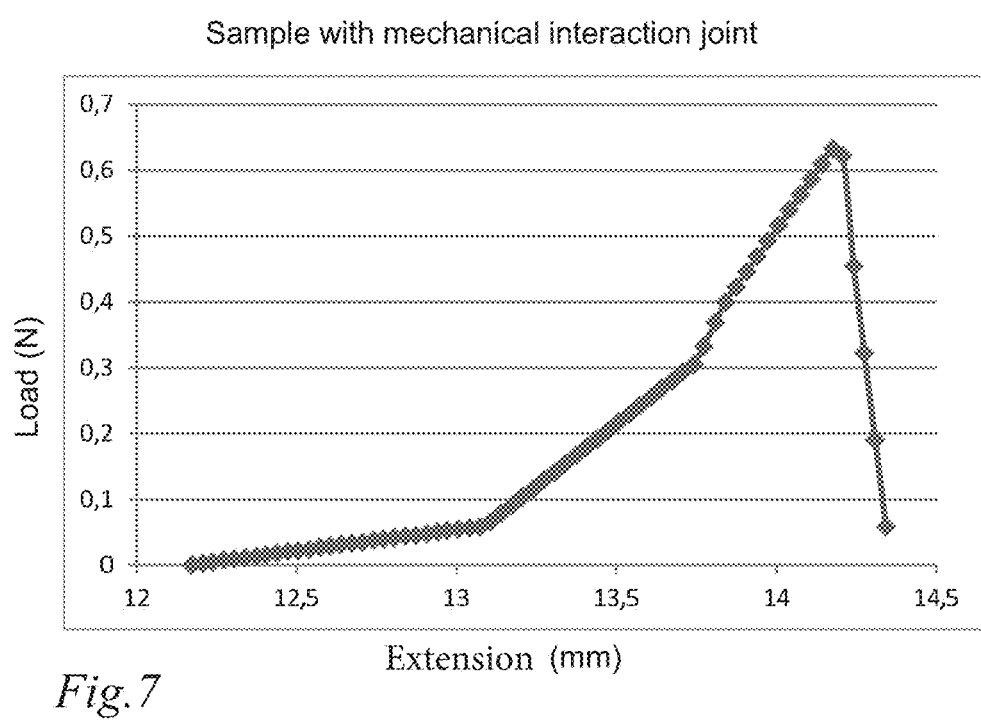
FIGS. 7-9 are graphs from test measurements.
Figure 8:
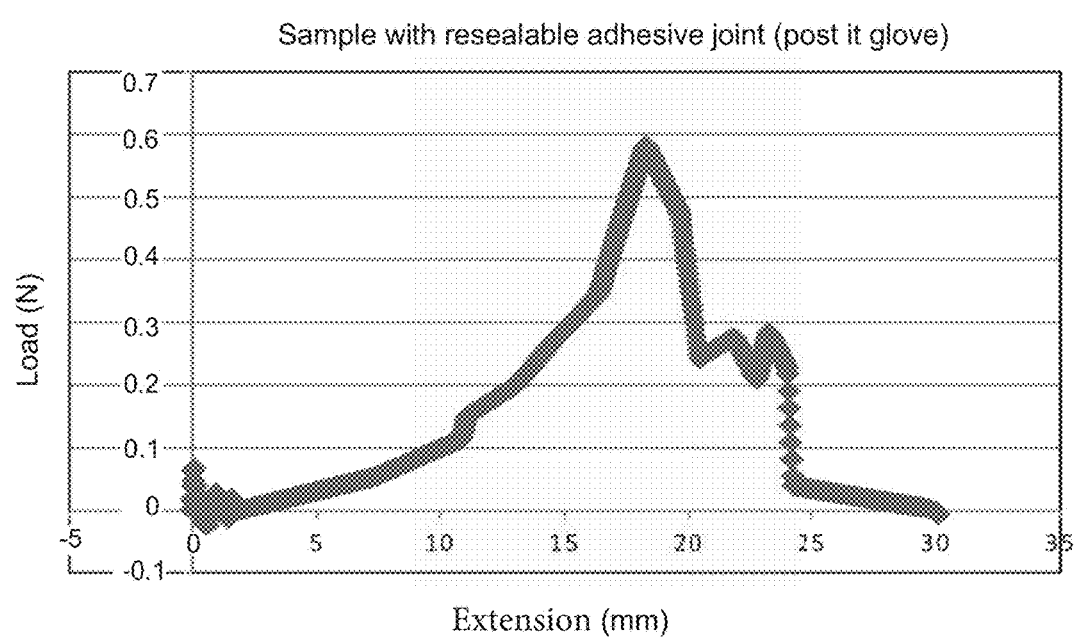
Figure 9:
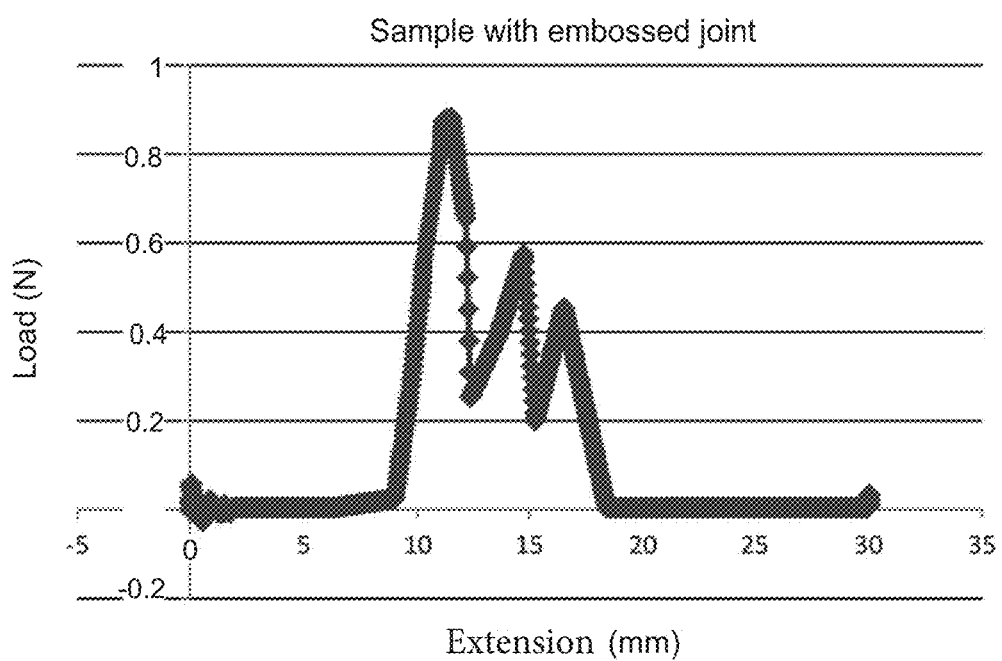

The results are set forth in FIGS. 7 to 10, wherein FIGS. 7 to 9 show test results in the form graphs from actual measurements. The x-axes are the pulling extension in mm and the y-axes represent the load in N. The samples tested were a sample with mechanical connection (FIG. 7), a sample with resealable adhesive connection (FIG. 8) and a sample with embossed connection (FIG. 9).

FIG. 10 is a table showing the maximum force and work for a number of samples for each type of connection.

When the results of the different tested samples as shown in FIGS. 7 to 10 are compared, it is realized that there is a difference between the present disclosure and the comparative samples, in particular for the performed work.

The samples of the present disclosure, i.e. the ones with mechanical interaction connections, show much lower mean work (Nmm/10 mm) for separating the layers than the samples connected by embossment and resealable adhesives.

The average sealing strength for the samples of the present disclosure is lower than for the samples with embossed connection. The average sealing strength of the samples with resealable connections is slightly higher than for the inventive samples, indicating that the mechanical connection may have a sealing strength that is similar to the resealable adhesive.

The invention claimed is:

1. A packaging unit for hygiene articles, the packaging unit being formed from a sheet of material, said sheet having an inner surface and an outer surface, said inner surface comprising an edge zone comprising an inner edge portion and an outer edge portion, wherein at least one of the outer edge portion and the inner edge portion comprises at least one region being provided with a resealable adhesive for closure and sealing of the packaging unit, thus forming an adhesive zone, said sheet having at least one folding axis, said folding axis dividing said sheet into a first region and a second region, wherein said sheet is folded about said at least one folding axis with said first region and said second region in an overlapping configuration, thereby providing a packaging unit of overlapping sheet layers, wherein the packaging unit comprises a zone in which overlapping outer edge portions of the sheet layers are adhesive-free and are at least partially connected to each other by a mechanical interaction providing an elongated joint with a width of 0.05 to 0.5 mm providing a sealing strength of 0.2 to 1.5 N as measured according to the test method as described in the specification.

2. The packaging unit according to claim 1, wherein the sealing strength is 0.2 to 1.1 N.

3. The packaging unit according to claim 1, wherein work for separating the sheet layers connected to each other by the mechanical interaction is 0.2 to 0.8 Nmm/10 mm, as measured according to the test method as described in the specification.

4. The packaging unit according to claim 1, wherein one of said inner edge portion and said outer edge portion of said edge zone of said first region is provided with the resealable adhesive, thus forming a first adhesive zone, and the other of said inner edge portion and said outer edge portion of said edge zone of said first region is adhesive-free; and wherein said inner edge portion or said outer edge portion of said edge zone of said second region corresponding to an adhesive-carrying edge portion of said first region is adhesive-free, such that when said sheet is folded about a first folding axis, said edge portions carrying resealable adhesive in said first region are brought in contact with said adhesive-free edge portions in said second region.

5. The packaging unit according to claim 4, wherein a distance between said first folding axis and said first adhesive zone is 1-20 mm.

6. The packaging unit according to claim 4, wherein one of said inner edge portion and said outer edge portion of said edge zone of said second region complementary to said adhesive-carrying edge portion of said first region is adhesive-free.

7. The packaging unit according to claim 4, wherein one of said inner edge portion and said outer edge portion of said edge zone of said second region complementary to said adhesive-carrying edge portion of said first region is provided with the resealable adhesive, thus forming a second adhesive zone.

8. The packaging unit according to claim 7, wherein a distance between said at least one first folding axis and said second adhesive zone is 1-20 mm.

9. The packaging unit according to claim 1, wherein said sheet has a longitudinal direction and a transverse direction and is of a substantially rectangular shape, and comprises longitudinal edges and transverse edges and sheet corner portions, wherein said at least one folding axis is at least one transversely extending folding axis, said edge zones being arranged along said longitudinal edges.

10. The packaging unit according to claim 9, wherein at least one of said corner portions is free from any adhesive for closure of the packaging unit.

11. The packaging unit according to claim 10, wherein when the packaging unit is folded, the overlapping sheet layers each have corner portions that are free from any adhesive for closure of the packaging unit.

12. The packaging unit according to claim 10, wherein said sheet comprises a first transverse edge zone and a second transverse edge zone, and wherein at least a portion of at least one of said first transverse edge zone and said second transverse edge zone is provided with resealable adhesive.

13. The packaging unit according to claim 1, wherein said sheet has two folding axes dividing said sheet into said first region, said second region and a third region, said sheet being folded along said two folding axes with said first region, said second region and said third region in an overlapping configuration of three layers, wherein outer edge portions of the three layers are at least partly connected to each other by the mechanical interaction.

14. The packaging unit according to claim 13, wherein one of said inner edge portion and said outer edge portion of said edge zone of said third region is provided with resealable adhesive, thus forming a third adhesive zone.

15. The packaging unit according to claim 14, wherein a distance between a second of said two folding axes and said third adhesive zone is 1-20 mm.

16. The packaging unit according to claim 13, wherein the two folding axes comprise a first folding axis and a second folding axis, dividing said sheet into said first region, said second region and said third region, and wherein said inner edge portion and said outer edge portion of said edge zone of said third region are adhesive-free, wherein said inner edge portion and said outer edge portion of said edge zone of said second region are provided with resealable adhesive.

17. The packaging unit according to claim 1, wherein the sheet is a single-ply material.

18. The packaging unit according to claim 17, wherein the single-ply material is of polyolefin.

19. The packaging unit according to claim 1, wherein the packaging unit comprises one or more sync marks for indication of a positioning of the sheet during manufacturing of the packaging unit.

20. The packaging unit according to claim 1, wherein said resealable adhesive is a pressure-sensitive hot melt adhesive.

21. The packaging unit according to claim 1, wherein said packaging unit is reclosable.

22. The packaging unit according to claim 1, wherein the inner surface comprises a center zone that comprises a portion provided with one of a release agent and a release liner.

23. The packaging unit according to claim 1, wherein the packaging unit comprises a hygiene article.

24. A method of forming a packaging unit for hygiene articles, the packaging unit being formed from a blank of an elongated sheet of material, the method comprising the steps of:
  providing said elongated sheet of material comprising at least two packaging unit sections for forming two packaging units, said elongated sheet of material having a first surface and a second surface, the first surface comprising an inner surface of each packaging unit and the second surface comprising an outer surface of each packaging unit, wherein the elongated sheet of material comprises at least one folding axis extending in a machine direction, said at least one folding axis dividing said elongated sheet of material into a first blank region and a second blank region;
  applying a resealable adhesive on an edge zone portion of the inner surface of each packaging unit section;
  folding said elongated sheet of material along said at least one folding axis with said first blank region and said second blank region in an overlapping configuration to provide a folded blank of overlapping sheet layers, and
  cutting the folded blank into two or more single packaging units by a use of a cutting and sealing tool,
  whereby packaging units are formed, each formed packaging unit comprises said inner surface and said outer surface, an inner edge portion and an outer edge portion, wherein at least one of the outer edge portion and the inner edge portion comprises at least one region being provided with said resealable adhesive forming an adhesive zone, the resealable adhesive being provided for closure and sealing of each packaging unit, wherein the packaging units each comprises a zone in which overlapping outer edge portions of sheet layers of each packaging unit are adhesive-free and are at least partially connected to each other by a mechanical interaction providing an elongated joint with a width of 0.05 to 0.5 mm providing a sealing strength of 0.2 to 1.5 N as measured according to the test method as described in the specification.

25. The method according to claim 24, wherein the sealing strength is 0.2 to 1.1.

26. The method according to claim 24, wherein average work for separating the sheet layers connected to each other by the mechanical interaction is 0.2 to 0.8 Nmm/10 mm, as measured according to the test method as described in the specification.

27. The method according to claim 24, wherein the method, prior to the folding step, comprises:
  applying a release agent on said first surface on a portion of each center zone of a packaging unit section;
  applying an adhesive on the portion with the release agent, and
  applying a hygiene article to said adhesive applied on the release agent.

28. The method according to claim 24, wherein the method, prior to the folding step, comprises:
  attaching a release liner on the first surface on a portion of each center zone of a packaging unit section, and
  connecting a hygiene article to the release liner by the use of fastening means.

29. The method according to claim 24, wherein each packaging unit section has a longitudinal direction and a transverse direction, and is of a substantially rectangular shape and comprises longitudinal edges and transverse edges and sheet corner portions.

30. The method according to claim 29, wherein at least one of said sheet corner portions is free from any adhesive for closure of the packaging unit.

31. The method according to claim 30, wherein when the formed packaging unit is folded, the overlapping sheet layers each have corner portions that are free from any adhesive for closure of the packaging unit.

32. The method according to claim 24, wherein said elongated sheet of material has two folding axes dividing said elongated sheet of material into said first blank region, said second blank region and a third blank region, said elongated sheet of material being folded along said two folding axes with said first blank region, said second blank region, and said third blank region in an overlapping configuration of three layers, wherein the cutting step provides a packaging unit with three packaging unit layers, wherein the outer edge portions of the three layers are at least partially connected to each other by the mechanical interaction.

33. The method according to claim 24, wherein the sheet is a single-ply material.

34. The method according to claim 33, wherein the single-ply material is of polyolefin.

35. The method according to claim 24, wherein an alternate pattern of the resealable adhesive and non-adhesive portions is applied along the inner edge portion and the outer edge portion of the edge zones for complementary attachment between resealable adhesive portions and the non-adhesive portions in the formed folded packaging unit.

36. The method according to claim 24, wherein the elongated sheet of material comprises one or more sync marks for indication of a positioning of the elongated sheet of material during manufacturing the packaging unit.

37. The method according to claim 24, wherein said resealable adhesive is a pressure-sensitive hot melt adhesive.

38. The method according to claim 24, wherein said packaging unit is reclosable.

* * * * *